(12) United States Patent
Kupferschmid et al.

(10) Patent No.: US 11,102,454 B2
(45) Date of Patent: Aug. 24, 2021

(54) IMAGE RELAYING DEVICE AND IMAGE DETECTING DEVICE

(71) Applicant: KARL STORZ SE & Co KG, Tuttlingen (DE)

(72) Inventors: Markus Kupferschmid, Emmingen-Liptingen (DE); Daniel Ulmschneider, Nendingen (DE); Andreas Heni, Fridingen (DE); Lawrence Natusch, Seitingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 14 days.

(21) Appl. No.: 15/918,709

(22) Filed: Mar. 12, 2018

(65) Prior Publication Data

US 2018/0270453 A1   Sep. 20, 2018

(30) Foreign Application Priority Data

Mar. 14, 2017   (DE) .......................... 102017105354.9

(51) Int. Cl.
*H04N 13/00* (2018.01)
*H04N 7/18* (2006.01)
(Continued)

(52) U.S. Cl.
CPC ............. *H04N 7/181* (2013.01); *A61B 1/002* (2013.01); *A61B 1/00009* (2013.01);
(Continued)

(58) Field of Classification Search
CPC .. H04N 7/181; H04N 13/243; A61B 1/00009; A61B 1/00059; A61B 1/00096;
(Continued)

(56) References Cited

U.S. PATENT DOCUMENTS 5,557,454 A    9/1996 Takahashi
5,720,706 A    2/1998 Takahashi
(Continued)

FOREIGN PATENT DOCUMENTS

DE         4405102 A1    8/1994
DE    102006017003 A1   10/2007
(Continued)

OTHER PUBLICATIONS

Rodriguez, C. J., Extended European Search Report for European Application No. 18161704.4-1124, dated Sep. 27, 2018, pp. 1-16, Munich, Germany.

*Primary Examiner* — Frank F Huang
(74) *Attorney, Agent, or Firm* — Michael Joseph Loi; David Noel Villalpando

(57) ABSTRACT

An image relaying device comprises a shaft, an objective lens at a distal end of the shaft, an optically transparent window region in a proximal end region of the image relaying device, an optical system in the shaft, the optical system relaying an image produced by the objective lens to the proximal end region in a way that the relayed image can be captured through the window region. The optical system's optical axis at the window region is orthogonal or substantially orthogonal to the optical system's optical axis in the shaft. An optical instrument makes use of a plurality of these image relaying devices and a corresponding plurality of image sensors where the optical path length of each image relaying device may be independently adjusted to correct for optical inconsistencies in the elements of each relaying device.

14 Claims, 6 Drawing Sheets

(51) Int. Cl.
*G02B 23/24* (2006.01)
*A61B 1/00* (2006.01)
*A61B 1/002* (2006.01)
*A61B 1/04* (2006.01)
*H04N 13/243* (2018.01)
*A61B 1/055* (2006.01)

(52) U.S. Cl.
CPC ...... *A61B 1/00059* (2013.01); *A61B 1/00096* (2013.01); *A61B 1/00188* (2013.01); *A61B 1/00193* (2013.01); *A61B 1/042* (2013.01); *A61B 1/055* (2013.01); *G02B 23/2415* (2013.01); *G02B 23/2446* (2013.01); *G02B 23/2484* (2013.01); *H04N 13/243* (2018.05); *G02B 23/2453* (2013.01)

(58) Field of Classification Search
CPC . A61B 1/00188; A61B 1/00193; A61B 1/002; A61B 1/042; A61B 1/055; G02B 23/2415; G02B 23/2446; G02B 23/2484; G02B 23/2453
See application file for complete search history.

(56) References Cited

U.S. PATENT DOCUMENTS

| | | | | |
|---|---|---|---|---|
| 6,025,873 | A | 2/2000 | Nishioka | |
| 6,537,208 | B1* | 3/2003 | Konno | A61B 1/00188 348/340 |
| 6,643,396 | B1* | 11/2003 | Hendriks | G01C 11/06 382/154 |
| 7,101,334 | B2* | 9/2006 | Takahashi | A61B 1/00193 348/45 |
| 2005/0197533 | A1* | 9/2005 | May | A61B 1/00071 600/164 |
| 2009/0292170 | A1 | 11/2009 | Boebel | |
| 2014/0071444 | A1 | 3/2014 | Matsumoto | |
| 2016/0255324 | A1 | 9/2016 | Kazakevich | |
| 2017/0112369 | A1 | 4/2017 | Czupalla | |
| 2018/0367786 | A1* | 12/2018 | Furst | A61B 1/00006 |

FOREIGN PATENT DOCUMENTS

| | | |
|---|---|---|
| DE | 102011119608 A1 | 5/2013 |
| DE | 102014115738 A1 | 5/2016 |

\* cited by examiner

IMAGE RELAYING DEVICE AND IMAGE DETECTING DEVICE

CROSS-REFERENCE TO RELATED APPLICATIONS

This application claims priority to German Application No. 102017105354.9 filed Mar. 14, 2017, incorporated herein by reference.

FIELD OF THE INVENTION

The present invention refers to an endoscope, an exoscope or another image relaying device and to an image detecting device detecting or sensing or capturing an image relayed by an image relaying device. The invention further concerns devices configured to relay or detect stereo images comprising at least a first image to be provided to a left eye of a user and a second image to be provided to a right eye of the user, thereby producing a three-dimensional impression.

BACKGROUND OF THE INVENTION

An exoscope is an image relaying device configured for being positioned and used outside a human or animal body. Like a surgical microscope, or operating microscope, an exoscope is generally used for imaging of objects at or close to the surface of the body and visible from outside. In many cases, an exoscope is smaller than a surgical microscope. In many cases, an exoscope is generally used for a larger object distance than a surgical microscope is. Unlike an endoscope, an exoscope may not be adapted for being inserted, through a natural or artificial orifice, into a cavity but is configured to operate outside the body. A borescope is similar to an endoscope but generally adapted for technical applications rather than for medical applications.

Conventional stereoscopic endoscopes or exoscopes comprise two objective lenses and two image sensors at their distal ends. Other stereo endoscopes or stereo exoscopes comprise two objectives at their distal ends, two image relaying systems relaying images produced by the objective lenses to their proximal end, and two image sensors at their proximal end. Other conventional stereo endoscopes comprise two objective lenses at their distal end, two image relaying systems relaying images produced by the objective lenses to their proximal end, and two parallel interfaces at their proximal end allowing a mechanical and optical coupling of a stereo camera with two image sensors to the proximal end of the stereo endoscope.

For many applications, there are good reasons not to integrate image sensors into an endoscope or into an exoscopes, in particular regarding costs of manufacture and repair, adaptability to different applications with different hardware requirements, and sterilization. When the image sensing or image detecting device is separable from the image relaying device, the interface between both devices and the compensation of variations within the manufacturing tolerance provides particular challenges.

An object of the present invention is to provide an improved endoscope or exoscope or other image relaying device and an improved image detecting device, in particular facilitating compensation for variations of characteristics of components and providing a high quality interface between both devices.

BRIEF SUMMARY OF THE INVENTION

Embodiments of the present invention concern themselves in part with providing an interface between an image relaying device and an image detecting device that is, compared to conventional devices, rotated by a given angle, for example, 90 degrees. Light from an object to be observed or imaged travels parallel to a shaft of the image relaying device, is reflected in a proximal end region of the device, and passes a window travelling in a direction orthogonal to the longitudinal axis of the shaft. A window in a proximal end region of the image relaying device through which the light leaves the image relaying device and a window of the image detecting device through which the light enters the image detecting device can be parallel to each other and also parallel to the longitudinal axis of the shaft of the image relaying device.

An image relaying device comprises a shaft, an objective lens at a distal end of the shaft, an optically transparent window region in a proximal end region of the image relaying device, and an optical system in the shaft. The optical system relays an image produced by the objective lens to the proximal end region such that the relayed image can be captured through the window region, wherein the optical system's optical axis at the window region is orthogonal or substantially orthogonal to the optical system's optical axis in the shaft.

The image relaying device may be an endoscope, borescope or an exoscope for medical or technical applications. The shaft can be rigid and straight or curved, or flexible. The objective lens at the distal end of the shaft can be configured for a direction of view parallel to the longitudinal axis of a shaft or for any other predetermined constant or variable direction of view.

The optically transparent window region is, in particular, at least a part of an opening of a casing, or housing of the image relaying device. This opening is, in general, hermetically closed by an optically transparent window element made of glass, sapphire or any other optically transparent material. The proximal end region of the image relaying device can be a proximal end region of the shaft. As an alternative, the proximal end region of the image relaying device can have a cross section different from, and, in particular, larger than the cross section of the shaft.

In case of a rigid and straight shaft, the optical system comprises, for example, a series of rod lenses or other relay lens units wherein each relay lens unit produces, from a first real intermediate image distal to the relay lens unit, a second real intermediate image proximal to the relay lens unit. The most proximal real intermediate image can be orthogonal or parallel to the optical system's optical axis in the shaft. The optical system can be configured to produce, from the most proximal real intermediate image, a virtual image which can be captured by a camera. As an alternative, the optical system can be configured to produce a real image outside, or downstream from, the optically transparent window region at a place where the image sensor of an image detecting device can be placed. The optical system's optical axis at the window region can be orthogonal or substantially orthogonal or, as an alternative, not parallel to the optical system's optical axis in the shaft.

In an image relaying device as described herein, the optical system can comprise a reflecting interface bending the optical system's optical axis. The reflecting interface can be a surface of a mirror (i.e. an interface between air or another gas or vacuum or glass and a thin metal layer). As an alternative, the reflecting interface can be a surface of a prism or an interface between two prisms made of materials with different refractive indices, wherein total internal reflection occurs at the interface. The angles between the reflecting interface and each arm of the optical system's optical axis are, in general, 45 degrees. The reflecting interface is, in general, arranged between the proximal end of the most proximal rod lens or other relay unit and the optically transparent window region. In general, no light refracting element is situated between the reflecting interface and the optically transparent window region.

An image relaying device as described herein can further comprise an adjustment mechanism facilitating adjustment of the position of the reflecting interface. The adjustment mechanism generally facilitates adjustment of the position of the reflecting interface at or near the end of manufacture or during maintenance or repair of the image relaying device or at some other time post manufacture. After adjustment of the adjustment mechanism, the adjustment mechanism can be sealed or blocked as a final or near-final step of manufacture or maintenance or repair. The adjustment mechanism generally supports the reflecting interface (i.e. the mirror or prism comprising the reflecting interface). For example, the adjustment mechanism may comprise a sliding carriage which can be moved in one direction along a rail or another structure. The adjustment mechanism may also comprise a screw wherein a rotation of the screw causes a displacement of the reflecting interface.

Characteristics of rod lenses or other components of the optical system are dispersed within a non-punctiform region of manufacturing tolerance, or engineering tolerance. As a consequence of dispersion of characteristics, the position of the most proximal real intermediate image rarely corresponds exactly to the original design. The ability to apply an adjustment to the position of the reflecting interface allows for a compensation of the position of the most proximal image produced by the optical system. In this way, the position of the most proximal (real or virtual) image produced by the optical system of an image relaying device can be adjusted precisely to an optimum design position. With this adjustment or compensation, the image relaying device provides an improved interface to an image detecting device.

In an image relaying device as described herein, the adjustment mechanism can facilitate translational displacement of the reflecting interface in a direction not parallel to the reflecting interface.

In an image relaying device as described herein, the adjustment mechanism can facilitate translational displacement of the reflecting interface in a direction parallel to the longitudinal axis of the shaft.

In an image relaying device as described herein, the adjustment mechanism can facilitate translational displacement of the reflecting interface in a direction parallel to the optical system's optical axis in the shaft or at the window region.

Translational displacement of the reflecting interface in a direction not parallel to the reflecting interface alters the length of the optical path from the objective lens along the optical system to the window region. A translational displacement of the reflecting interface in a direction parallel to the longitudinal axis of the shaft can be achieved with a sliding carriage moving along any kind of rail parallel to the shaft. A translational displacement of the reflecting interface in any other predetermined direction can be achieved with a sliding carriage moving along any kind of rail parallel to this predetermined direction.

An image relaying device as described herein can comprise a position indicator providing information comprising the position of the reflecting interface to a receiver outside the image relaying device. This position indicator can comprise a magnet at the adjustment mechanism. The magnetic field produced by the magnet can be sensed or detected outside the casing of the image relaying device. In particular, a Hall effect sensor (Hall sensor) or another sensor or detector detecting the flux density and/or direction of the magnetic field produced by the magnet can be used to determine the position of the magnet and, thereby, the position of the adjustment mechanism and the reflecting interface. The position indicator may also or alternately comprise a linear bar code or a two dimensional matrix code wherein the position of the reflecting interface is encoded.

In an image relaying device as described herein, the optical system can be configured to provide a real image outside a casing of the image relaying device. The optical system may be configured to provide a real image in the vicinity of the window region, for example, a few millimeters or several millimeters outside the window region. This real image can be detected or sensed by an image sensor of an image detecting device comprising no curved refracting or reflecting surface.

In an image relaying device as described herein, the window region is a first window region and the optical system is a first optical system, wherein the image relaying device further comprises a second optically transparent window region in the proximal end region of the image relaying device and a second optical system in the shaft, wherein the second optical system is similar to the first optical system, wherein the second optical system relays an image produced by the objective lens or by another objective lens to the proximal end region in such a way that the relayed image can be captured through the second window region, wherein the second optical system's optical axis at the second window region is orthogonal or substantially orthogonal to the second optical system's optical axis in the shaft and parallel to the first optical system's optical axis at the first window region.

An image relaying device as described herein can comprise two window regions and two similar optical systems, wherein the optical systems' optical axes at their respective window regions are parallel to each other. Both window regions can be arranged parallel and close to each other. In particular, both window regions can be part of the same optically transparent window element. As an alternative, the window regions can be formed by two different optically transparent window elements. These two different optically transparent window elements can be arranged parallel and/or close to each other or spaced apart from each other. In particular, both window elements can be arranged at opposite sides of the casing of the image relaying device. In the shaft, both optical systems are arranged parallel to each other and both optical systems' optical axes are parallel to each other. In general, both optical systems provide—within the limits of manufacturing tolerance—identical characteristics.

The image relaying device can also comprise more than two optical systems (for example three, four, or five optical systems) and a corresponding number of window regions, wherein all optical systems may provide—within the limits of manufacturing tolerance—identical characteristics.

In an image relaying device as described herein, the directions of propagation of light in the optical systems at their respective window regions can be opposite to each other. In general, the directions of propagation of light originating from the same observed object in the optical systems at their respective window regions are opposite to each other.

In an image relaying device as described herein, the two window regions can be formed by two different window elements which are parallel to each other and arranged at opposite sides of a casing of the image relaying device.

In particular, an image relaying device as described herein is may be an endoscope or an exoscope or a surgical microscope or a borescope or is part of an endoscope or an exoscope or a surgical microscope or a borescope.

An image detecting device for an image relaying device comprises an image sensor, a window element, wherein light passing the window element is detected by the image sensor, and a coupling mechanism for a separable mechanical coupling of the image detecting device to an image relaying device, wherein the image detecting device is configured to be coupled to an image relaying device in such a way that a longitudinal axis of a shaft of the image relaying device is parallel to the window element.

The image detecting device can be configured to be coupled to and functionally combined with an image relaying device as described herein. An image sensor is provided for detecting an image projected onto the image sensor (more particularly onto or into its light sensitive layer) and for generating an (analogue or digital, in particular electronic) image signal representing the detected image. As an example, the image sensor can be a CCD- or a CMOS-sensor with a matrix of pixels, or light sensitive elements. The image sensor can comprise a Bayer-filter, i.e. a matrix of red, green and blue filter elements in front of light sensitive elements. As an alternative, the image detecting device can comprise a number of image sensors and a number of dichroic filters, wherein the dichroic filters allow light within a respective predetermined range of wavelengths only to be detected by each image sensor.

The window of the image detecting device may be arranged parallel to the image sensor. The window can face the image sensor or be integral with the image sensor.

The coupling mechanism can comprise a recess in the casing of the image detecting device, wherein the shape of the recess corresponds to the shape of the proximal end of an image relaying device the image detecting device is provided for. The coupling mechanism can comprise a latching mechanism or a bayonet mechanism or a magnet mechanism allowing to repeatedly couple the image detecting device to an image relaying device and decouple the image detecting device from the image relaying device without damaging either of the devices.

An image detecting device as described herein can further comprise a receiver for receiving, from a position indicator of an image relaying device, information representing the position of a reflecting interface of the image relaying device. The receiver can be configured to receive the information when the image detecting device is coupled to the image relaying device or during the coupling procedure. The receiver can comprise a Hhall sensor or another sensor sensing the direction or flux density of a magnetic field or a bar code reader or a matrix code reader. A Hall sensor or another sensor sensing the direction or the flux density of a magnetic field allows for a determination of the position of a magnet inside the image relaying device. When the position of the reflecting interface inside the image relaying device is unambiguously coupled to the position or orientation of a magnet inside the image relaying device, the position of the reflecting interface can be deduced from the orientation or flux density of a magnetic field produced by the magnet. As an alternative, the position of the reflecting interface can be encoded in a bar code or a matrix code at the outer surface of the casing of the image relaying device, and the bar code reader or matrix code reader can read the encoded position.

An image detecting device as described herein can further comprise a frame positioning circuit determining, from the position information, the position of a region of the image sensor, wherein exclusively image data from within the region are read from the image sensor or exclusively image data from within the region are read from a memory or exclusively image data from within the region are transmitted to a display or exclusively image data from within the region are stored in a memory. The frame positioning circuit may be partially or entirely identical to an image evaluating circuit or to an image data processing circuit. When the reflecting interfaces of different image relaying devices are located at different positions, the images relayed by the image relaying devices are projected onto different regions of the image sensor of the image detecting device. This can be compensated by the frame positioning circuit electing the respective region of the image sensor in response to the position information.

An image detecting device as described herein can be configured to detect a real image provided by the image relaying device.

The image detecting device can be configured to be coupled to an image relaying device providing a real image outside the image relaying device. In this case, the image detecting device can comprise no curved refracting or reflecting interface. Rather, the image sensor can be positioned just behind the window element of the image detecting device. In particular, the image sensor can be integral with the window element of the image detecting device.

An image detecting device as described herein can comprise two image sensors, wherein the image detecting device is configured to receive, in a region between the image sensors, a proximal end region of an image relaying device comprising two optical systems simultaneously relaying two images, in a way that each of the images relayed by one of the two optical systems is received by one of the two image sensors. When the image detecting device comprises two image sensors and is configured to receive a proximal end region of an image relaying device in a region between the image sensors, the image detecting device comprises, in particular, two window elements.

The image detecting device can comprise more than two image sensors, for example three, four, or five image sensors. The image detecting device can be configured to be combined with an image relaying device comprising a corresponding number or a different number of optical systems.

An image detecting device as described herein can further comprise an image evaluating circuit comparing image signals provided by the two image sensors and calculating, from the comparison of the image signals, position information representing the relative positions of reflecting interfaces of the image relaying devices. When the reflecting interfaces in the optical systems of the image relaying device are positioned differently, a misalignment, or offset, of the images received by the image sensors results. From a comparison of the image signals, this offset can be calculated and can be used as a position information as described above. In particular, the position of regions of the image sensors (at least the position of a region of one image sensor) can be calculated, wherein exclusively image data from within this region of these regions are read, stored or transmitted.

DETAILED DESCRIPTION OF THE INVENTION

Figure 1:
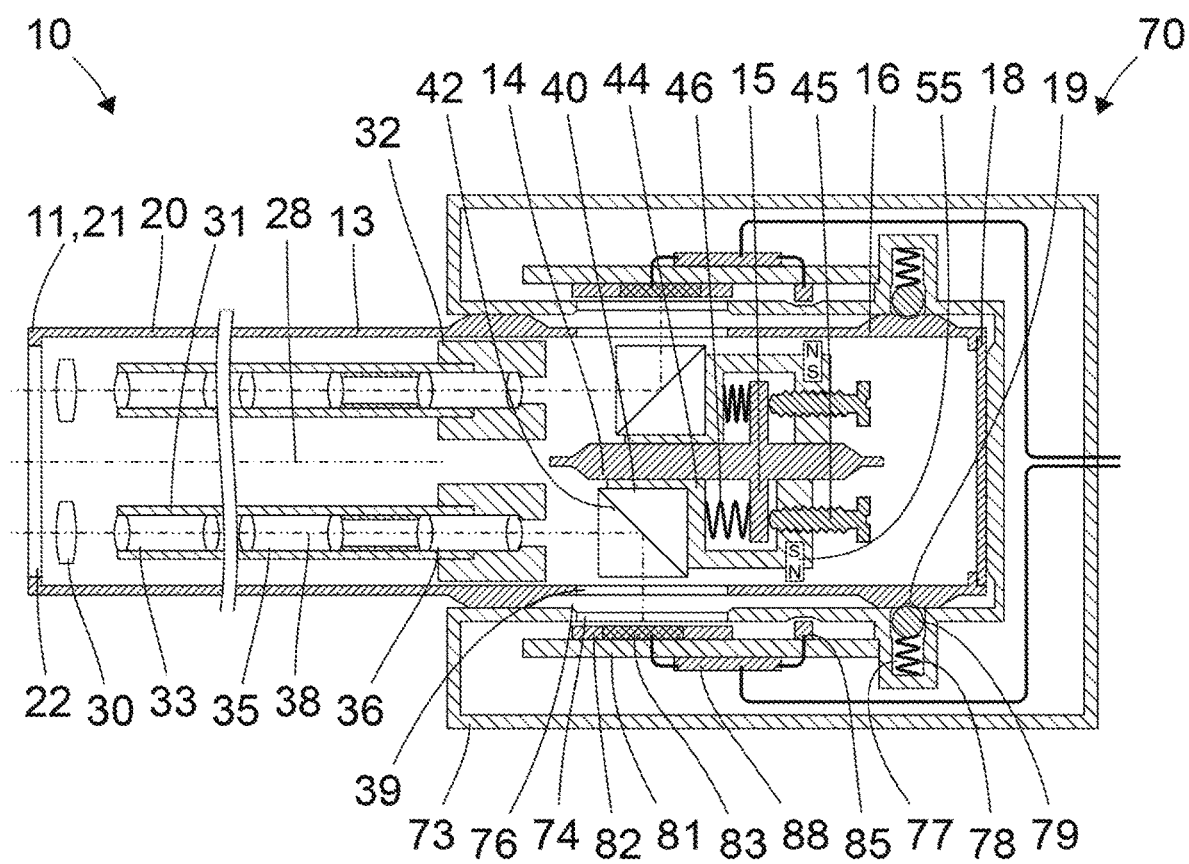
FIG. 1 shows a schematic representation of an image relaying device and an image detecting device.

FIG. 1 shows a schematic representation of an endoscope 10 and an image detecting device 70. More particularly, FIG. 1 shows a longitudinal section through the endoscope 10 and the image detecting device 70. Cross sections of non-transparent objects are shown as hatched areas, cross sections of optically transparent elements (window elements, lenses, prisms) are not hatched.

The endoscope 10 is one example of an image relaying device according to the present invention. The endoscope 10 comprises a shaft 20. The distal end 21 of the shaft 20 forms the distal end 11 of the endoscope 10. The shape of the shaft 20 is essentially cylindrical with a circular, an elliptical or another cross sectional area. The axis of rotational symmetry of the outer surface of the shaft 20 or, in case of rotational non-symmetry, the line formed by the centers of the cross sectional areas, is called the longitudinal axis 28 of the shaft 20.

A proximal end region 16 of the endoscope can provide essentially the same cross section as the shaft 20 or a different cross section. In the configuration shown in FIG. 1, the proximal end region 16 of the endoscope 10 is positioned within a recess 76 of corresponding shape in the image detecting device 70.

The casing 13 of the example endoscope 10 shown in FIG. 1 comprises at least four openings all of which are hermetically closed. An opening at the distal end 21 of the shaft 20 is hermetically closed by an optically transparent window element 22. Two openings at opposite sides of the proximal end region 16 of the endoscope 10 are hermetically closed by optically transparent window elements 39. The optically transparent window elements 39 are arranged symmetrically with respect to the longitudinal axis 28 of the shaft 20. An opening at the proximal end face of the proximal end region 16 of the endoscope 10 is closed by a lid 18.

Within the casing 13 of the endoscope 10, two objective lenses 30 immediately proximal to the window element 22 at the distal end 21 of the shaft 20, a number of rod lenses 33, 35, 36 and two prisms 40 are arranged. Two tubes 31 are arranged in parallel inside the shaft 20. One of two end guides 32 is fixed to the proximal end of each tube 31. Each tube 31 holds a number of rod lenses 33, 35, 36. One of the objective lenses 30, the rod lenses 33, 35, 36 arranged in one of the tubes 31 and one of the two prisms 40 form a light path. Both light paths are essentially similar, and are arranged symmetrical with respect to a plane of symmetry, wherein the plane of symmetry is orthogonal to the sectional plane shown in FIG. 1 and comprises the longitudinal axis 28 of the shaft 20. Therefore, reference numerals refer to only one of the two light paths.

In each light path, the respective objective lens 30 produces a real image of an object observed by means of the endoscope 10. This real image produced by the objective lens 30 is relayed to the proximal end region 16 of the endoscope 10 by means of the rod lenses 33, 35, 36, wherein each rod lens or each rod lens unit comprising a pair of rod lenses produces, from a real intermediate image distal to the rod lens or rod lens unit, another real intermediate image proximal to the rod lens or rod lens unit. The (identical) optical axes of the objective lens 30 and the rod lens units 33, 35, 36 define the optical axis 38 of the light path. The prism 40 comprises a reflecting interface 42 at an angle of 45 degree with respect to the optical axis 38 of the light path upstream from (distal to) the reflecting interface 42 and at an angle of 45 degrees with respect to the optical axis 38 of the light path downstream from the reflecting interface 42. The reflecting interface 42 reflects the light transmitted by the objective 30 and the rod lens units 33, 35, 36 and, thereby, bends the optical axis 38 by 90 degrees. Upstream from the reflecting interface 42, the optical axis 38 of the light path is parallel to the longitudinal axis 28 of the shaft 20. Downstream from the reflecting interface 42, the optical axis 38 of the light path is orthogonal to the longitudinal axis 28 of the shaft 20. Downstream from the reflecting interface 42 the light path leaves the endoscope 10 through the respective window element 39 and the optical axis 38 of the light path crosses the respective window element 39.

Each of the prisms 40 is held, carried, or supported by a respective sliding carriage 44. Each sliding carriage 44 is slidably fixed to a rail 14 integral with or rigidly connected to the casing 13 of the endoscope 10. The rails 14 define a predetermined path parallel to the longitudinal axis 28 of the shaft 20 and inhibit any motion of the respective carriage 44 in any direction perpendicular to the rail 14.

At each sliding carriage 44, an adjusting screw 45 and a spring 46 (not shown in sectional view) are provided. One end of the adjusting screw 45 and one end of the spring 46 rest on a support 15 integral with or rigidly connected to the casing 13. The other end of the spring 46 rests at a surface of the sliding carriage 44 opposite to the support 15. The thread of the adjusting screw 45 engages in a corresponding thread in the sliding carriage 44. Therefore, any rotation of the adjusting screw 45 causes a translational displacement of the sliding carriage 44.

In the embodiment shown in FIG. 1, at each sliding carriage 44, a magnet 55 is provided producing a magnet field that can be sensed or detected outside the casing 13 of the endoscope 10.

A notch 19 is provided in the outer surface of the casing 13 of the endoscope 10. A bore 77 is provided in a region of the outer surface of the casing 73 of the image detecting device 70 which region faces the recess 73. In the bore 77, a helical spring 78 and a ball 79 are provided. In the configuration shown in FIG. 1, the helical spring 78 presses the ball 79 into the notch 19 in the outer surface of the casing 13 of the endoscope 10. The notch 19, the helical spring 78, and the ball 79 form a latching mechanism releasably fixing the proximal end region 16 of the endoscope 10 inside the recess 76 in the image detecting device 70.

Small clearance between the outer surface of the proximal end region 16 of the endoscope 10 and the inner surface of the recess 76 of the image detecting device 70 and the latching mechanism 19, 78, 79 guarantee a predetermined geometry of the entire system. In the example shown in FIG.

1, two latching mechanisms 19, 78, 79 are provided symmetrically. As an alternative, merely one latching mechanism 19, 78, 79, or one or more different latching mechanisms may be provided.

The casing 73 of the image detecting device 70 shown in FIG. 1 comprises, at opposites sides of the recess 76, two optically transparent window elements 74 hermetically or fluid tightly closing openings in the casing 73. Each window element 74 of the image detecting device 70 is positioned parallel and opposite to a respective window 39 of the endoscope 10. Behind each window element 74 of the image detecting device 70, i.e. inside the casing 73 of the image detecting device 70, a printed circuit board 81 with an image sensor 82, a Hall sensor 85 and a data processing unit 88 are provided in various embodiments. Each image sensor 82 is parallel to the respective window 74 and, in the configuration shown in FIG. 1, orthogonal to the optical axis 38 of one of the light paths of the endoscope 10. Each data processing circuit 88 may be coupled to the respective image sensor 82 and to the respective Hall sensor 85.

Characteristics of optical elements like the objective lenses 30 and the rod lens units 33, 35, 36 rarely precisely conform to their theoretical or design values. Rather, the characteristics are distributed within a region of engineering or manufacturing tolerances. As a consequence, the positions of the real intermediate images and of the most proximal real image to be captured by the image sensor 82 are distributed. Without any compensation, for example, by means of the sliding carriages 44 of the present invention, the most proximal real images produced by the most proximal rod lenses 36, as shown in the example of FIG. 1: would rarely be precisely within the planes of the image sensors 82 but almost always slightly upstream or slightly downstream from the planes of the image sensors 82. Thus, the image sensors would be located out of the focal plane for one or both of the light paths, and would capture blurred images in most cases.

In the endoscope 10 shown in FIG. 1, the distribution of the characteristics of the optical elements 30, 33, 35, 36 can be compensated for by adjusting the positions of the reflecting interfaces 42 by means of a rotation of the adjusting screws 45 and by the resulting displacements of the sliding carriages 44. When the positions of the reflective interfaces 42 are adjusted at the end of a manufacturing process of the endoscope 10, the proximal opening of the casing 13 can be closed by the lid 18. The lid 18 can be welded to the casing 13 for a hermetical closure.

As a result of the adjustment of the positions of the reflecting interfaces 42, the most proximate real images produced by the endoscope 10 are produced precisely in the planes of the image sensors 82. However, as can be seen from the positions of the optical axes 38 of the optical paths downstream from the reflecting interfaces 42, the adjustment of the positions of the reflecting interfaces 42 results in a lateral displacement of the images projected onto the image sensors 82.

This lateral displacement of the images projected by the endoscope 10 onto the image sensors 82 is compensated by the data processing circuits 88. Each data processing circuit 88 reads the sensor signal of the respective Hall sensor 85. From the sensor signals of the Hall sensors 85, the data processing circuits 88 can calculate the positions of the magnets 55 at the sliding carriages 44. From the calculated positions of the sliding carriages 44 the data processing circuits 88 can calculate the positions of the regions 83 of the image sensors 82 onto which the endoscope projects the images. Each data processing circuit 88 instructs the respective image sensor 82 to provide image data referring to the respective region only. As an alternative, all the image data of the image sensors 82 are read by the data processing circuits 88 but the data processing circuits 88 discard image data not referring to the selected regions 83 and merely provide image data referring to the selected regions 83 to a display.

Figure 2:
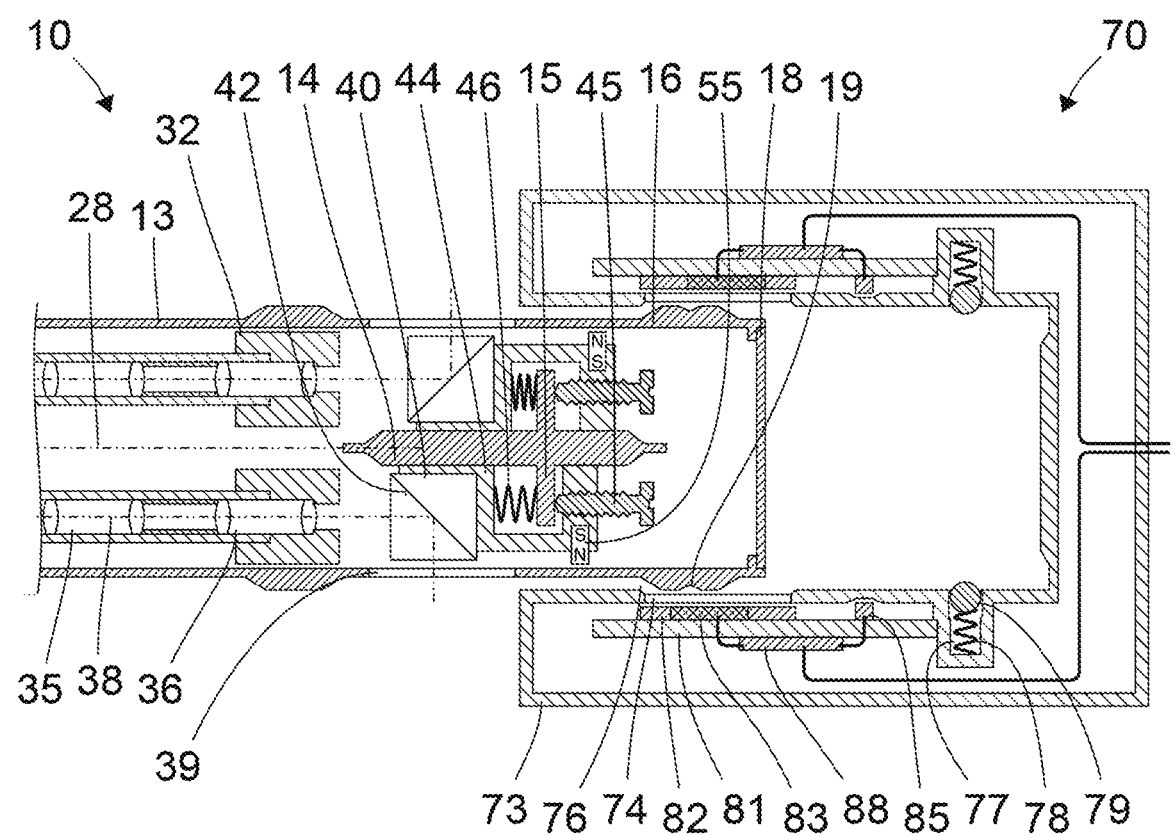
FIG. 2 shows a schematic representation of the image relaying device and the image detecting device shown in FIG. 1 in another configuration.

FIG. 2 shows a further schematic representation of the endoscope 10 and the image detecting device 70 described above with reference to FIG. 1. The sectional plane shown in FIG. 2 corresponds to the sectional plane of FIG. 1.

The configuration shown in FIG. 2 is different from the configuration shown in FIG. 1. In the configuration shown in FIG. 2, the proximal end region 16 of the endoscope 10 is only partially inserted into the recess 76 of the image detecting device 70. The configuration shown in FIG. 1 is an intermediate state temporarily existing when the image relaying device and the image detecting device are combined (to form the system and configuration shown in FIG. 1) or separated.

Figure 3:
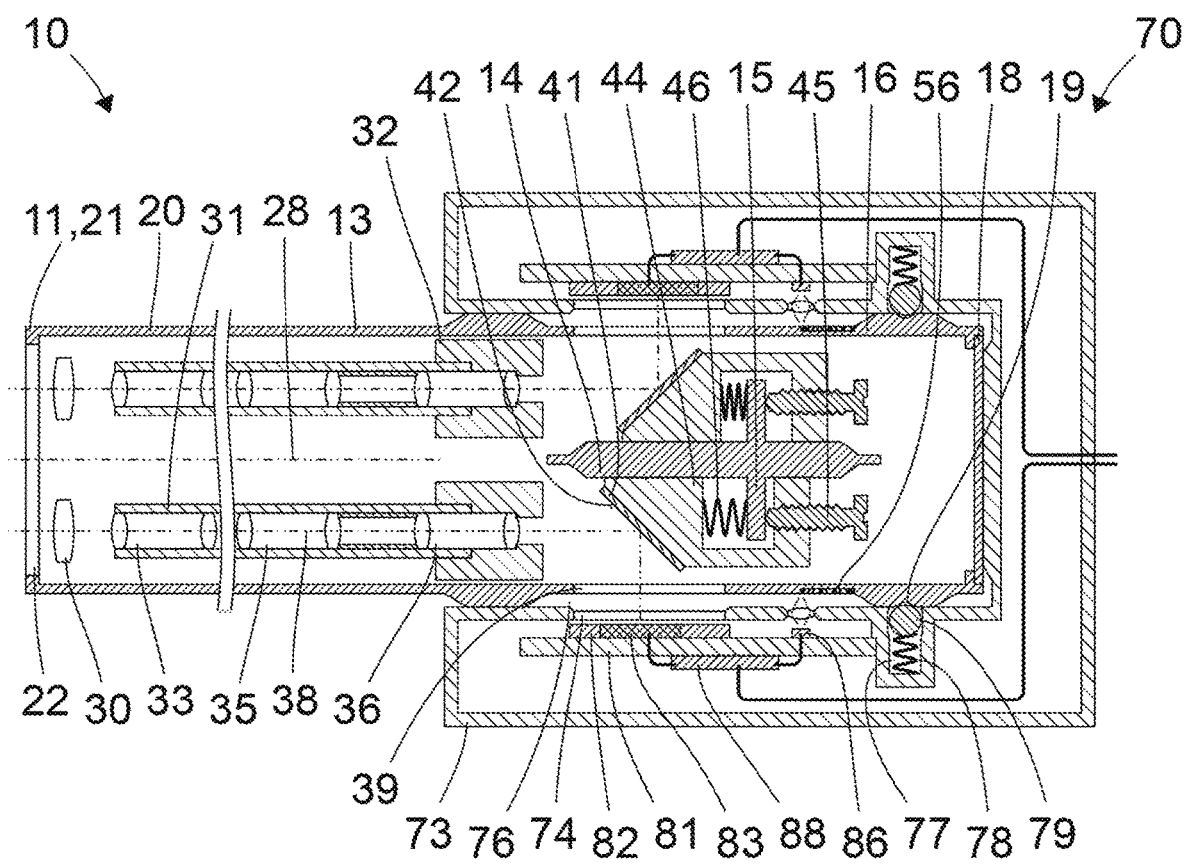
FIG. 3 shows a schematic representation of another image relaying device and another image detecting device.

FIG. 3 shows a schematic representation of a further endoscope 10 and a further image detecting device 70. The sectional plane of FIG. 3 corresponds to the sectional planes of FIGS. 1 and 2. With respect to many features, characteristics and functions, the endoscope 10 and the image detecting device 70 shown in FIG. 3 are similar to the endoscope and the image detecting device described above with reference to FIGS. 1 and 2. Below, in particular features, characteristics and functions of the endoscope 10 and the image detecting device 70 shown in FIG. 3 which are different from those of the endoscope and the image detecting device described above with reference to FIGS. 1 and 2 are described.

In contrast to the endoscope described above with reference to FIGS. 1 and 2, the endoscope 10 shown in FIG. 3 comprises a mirror 41 instead of a prism. The mirror 41 comprises a reflecting layer, for instance an aluminum or silver layer. The surface of this reflecting layer is a reflecting interface.

In contrast to the endoscope described above with reference to FIGS. 1 and 2, no magnets are provided at the sliding carriages 44 of the endoscope 10 shown in FIG. 3. Instead, a bar code or—as shown in FIG. 3—two bar codes 56 are provided at the outer surface of the casing 13 in the proximal end region 16 of the endoscope 10. These bar codes 56 numerically encode the positions of the reflecting interfaces 42 set by means of the adjusting screws 45 at the end of the manufacturing process.

In contrast to the image detecting device described above with reference to FIGS. 1 and 2, the image detecting device 70 shown in FIG. 3 comprises a bar code reader or—as shown in FIG. 3—two bar code readers 86. The bar codes 56 and the bar code readers 86 are arranged such that the bar code readers 86 can read the bar codes 56 when the proximal end region 16 of the endoscope 10 is inserted into the recess 86 of the image detecting device 70. The data processing circuits 88 receive the position information encoded in the bar codes 56 and read by the bar code readers 86 and, depending on the position information, select the regions 83 of the image sensors 82.

Figure 4:
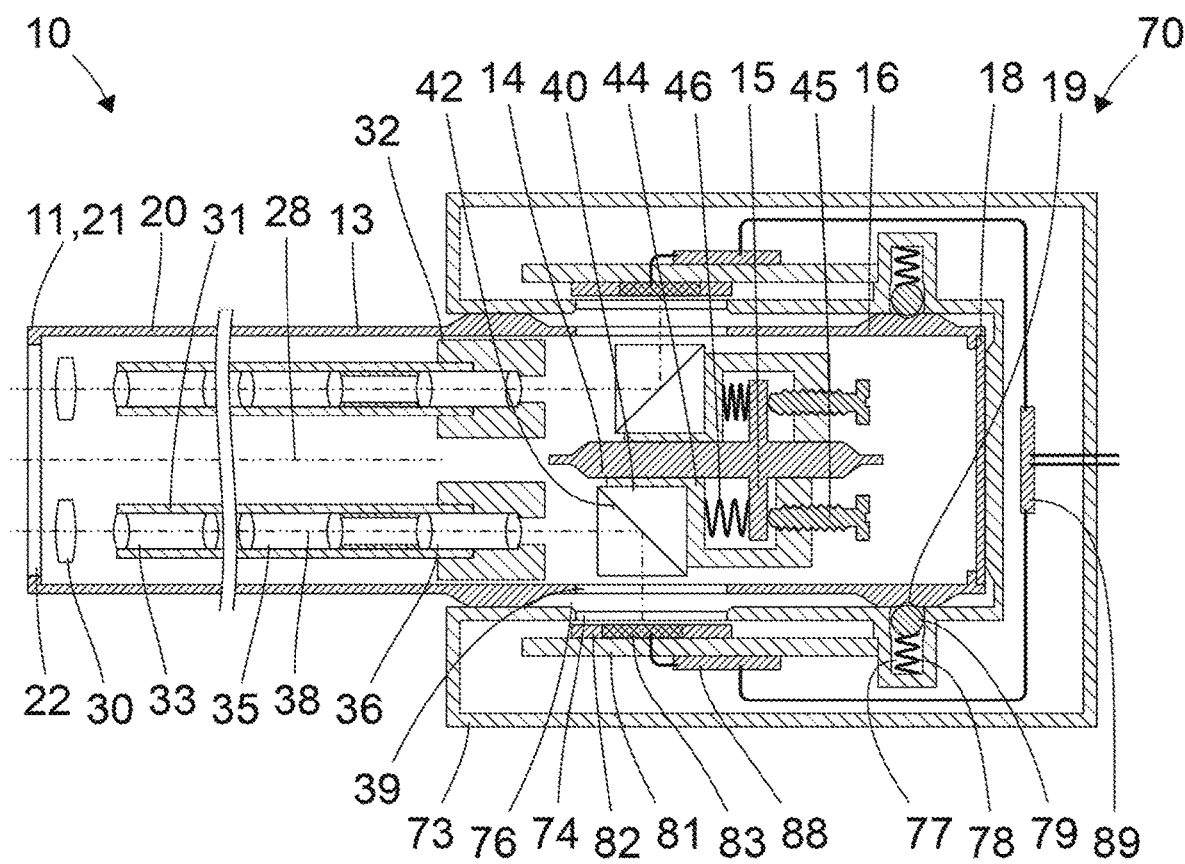
FIG. 4 shows a schematic representation of another image relaying device and another image detecting device.

FIG. 4 shows a schematic representation of a further endoscope 10 and a further image detecting device 70. The sectional plane shown in FIG. 4 corresponds to the sectional planes of the FIGS. 1 through 3. With respect to many features, characteristics and functions, the endoscope 10 and the image detecting device 70 shown in FIG. 4 are similar to the endoscopes and image detecting devices described above with reference to FIGS. 1 through 3. Below, in particular features, characteristics and functions of the endoscope 10 and the image detecting device 70 shown in FIG. 4 which are different from those of the endoscopes and the image detecting devices described above with reference to FIGS. 1 through 3 are described.

Similar to the endoscope described above with reference to FIG. 3, no magnets are provided at the sliding carriages of the endoscope 10 shown in FIG. 4. Furthermore, no bar code or other indicator provides information regarding the positions of the reflecting interfaces 42. Rather, the image detecting device 70 comprises an image evaluating circuit 89 comparing image data received from the image sensors 82. The image evaluating circuit 89 calculates, from the image data, the difference of the positions of the reflecting interfaces 42. The image evaluating circuit 89 provides corresponding position information to the data processing circuits 88 or to the image sensors 82 and causes them to exclusively provide image data referring to the regions 83 corresponding to the positions of the reflecting interfaces 42. As an alternative, the image evaluating circuit 89 receives image data from the entire image sensors 82 but discards image data not referring to the regions 83 and exclusively forwards image data referring to the regions 83 to a display.

The functionalities and capabilities and tasks of the data processing circuits 88 and the image evaluating circuit 89 can be distributed differently from the schematic representations in FIGS. 1 through 4.

Figure 5:
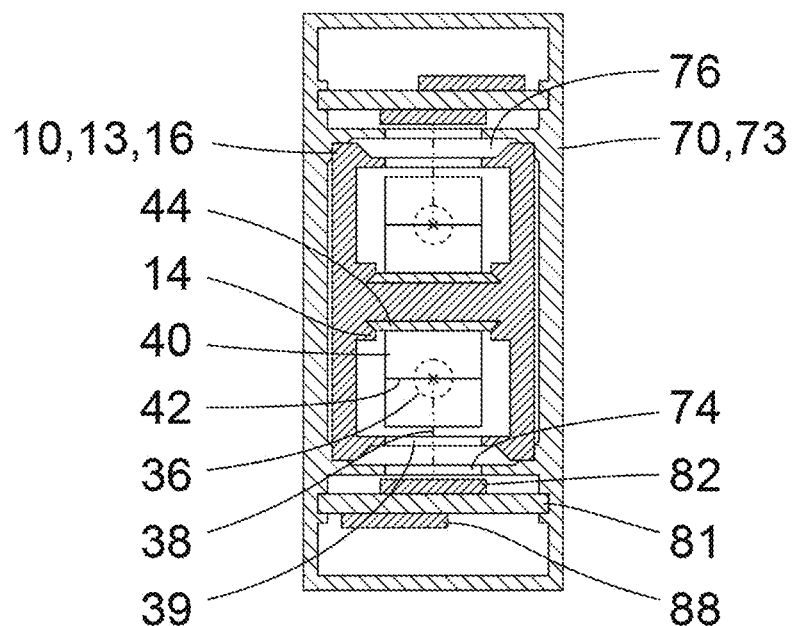
FIG. 5 shows another schematic representation of the image relaying device and the image detecting device shown in FIG. 1.

FIG. 5 shows a schematic sectional representation of the endoscope 10 and the image detecting device 70 described above with reference to FIGS. 1 and 2. The sectional plane of FIG. 5 is orthogonal to the sectional planes of FIGS. 1 and 2 and orthogonal to the longitudinal axis 28 of the shaft 20 (cf. FIGS. 1 and 2). Upstream from the reflecting interfaces 42, the optical axes 38 of the light paths are orthogonal to the sectional plane of FIG. 5, and downstream from the reflecting interfaces 42, the optical axes 38 of the light paths are parallel to the sectional plane of FIG. 5. FIG. 5 shows a configuration different from the configuration shown in FIGS. 1 and 2. Both prisms 40 are adjusted to the same longitudinal position, and, downstream from the reflecting interfaces, the optical axes 38 of both light paths are in the sectional plane of FIG. 5.

In the embodiments described above with reference to FIGS. 3 and 4, sections corresponding to the section shown in FIG. 5 are substantially similar to the section shown in FIG. 5.

The rod lens units 33, 35, 36 (cf. FIGS. 1, 2) are not in the sectional plane of FIG. 5. However, the projections of the most proximal rod lenses 36 are schematically represented by broken lines in FIG. 5.

The sectional plane of FIG. 5 intersects the inclined reflecting interface 42. The positions of the optical axes 38 upstream from the reflecting surface 42 are indicated by crosses at the centers of the rod lenses 36, and the optical axes 38 downstream from the reflecting surfaces 42 are represented by broken lines.

Figure 6:
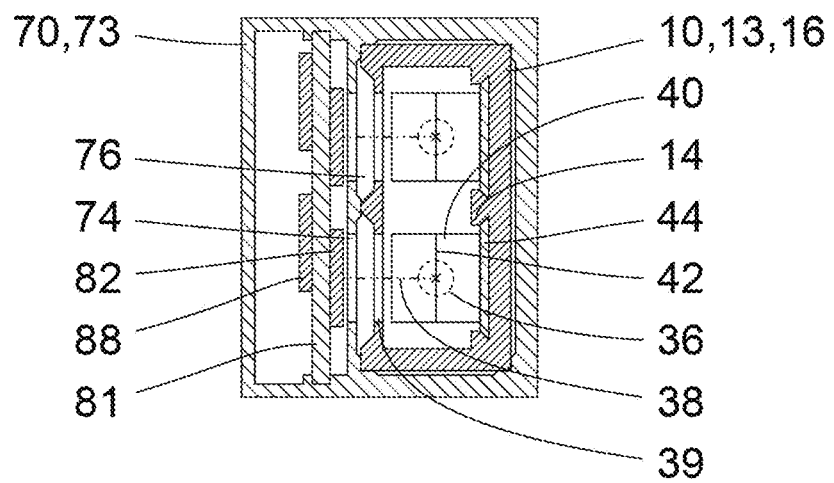
FIG. 6 shows a schematic representation of another image relaying device and another image detecting device.

FIG. 6 shows a schematic sectional representation of a further endoscope 10 and a further image detecting device 70. The sectional plane of FIG. 6 corresponds to the sectional plane of FIG. 5. The configuration shown in FIG. 6 corresponds to the configuration shown in FIG. 5 (both prisms 40 adjusted to the same longitudinal positions).

With respect to many features, characteristics and functions, the endoscope 10 and the image detecting device 70 shown in FIG. 6 are similar to the endoscopes and the image detecting devices, respectively, described above with reference to FIGS. 1 through 5. Below, in particular features, characteristics and functions of the endoscope 10 and the image detecting device 70 shown in FIG. 6 which are different from those of the endoscope and the image detecting device described above with reference to FIGS. 1 through 5 are described.

In contrast to the endoscopes described above with reference to FIGS. 1 through 5, in the endoscope 10 shown in FIG. 6, the directions of propagation of light from an object to the image sensors 82 are parallel not only upstream but also downstream from the reflecting interfaces 42. Hence, the window elements 39 of the endoscope 10 are not positioned at opposite sides of the casing 13 of the endoscope 10, but side by side, and the image sensors 82 of the image detecting device 70 are not positioned at opposite sides of the recess 76, but side by side.

One consequence of the configuration shown in FIG. 6 is that the images captured by the image sensors 82 can be compared more easily. Different positions of the reflecting interfaces 42 (cf. FIGS. 1 through 4) cause an offset of both images in a direction orthogonal to the stereo basis. This offset does not interfere with the disparity caused by the distance of the object.

Another consequence of the configuration shown in FIG. 6 is that both image sensors 82 can be provided on the same printed circuit board 81. Additionally, in some embodiments of the general configuration shown in FIG. 6, a single image sensor with an active area of adequate dimensions to capture both images relayed by the reflecting interfaces 42 on a single active area could be used rather than using two distinct image sensors 82. The individual images could then be resolved by a single image processing circuit 88 or by other means.

Figure 7:
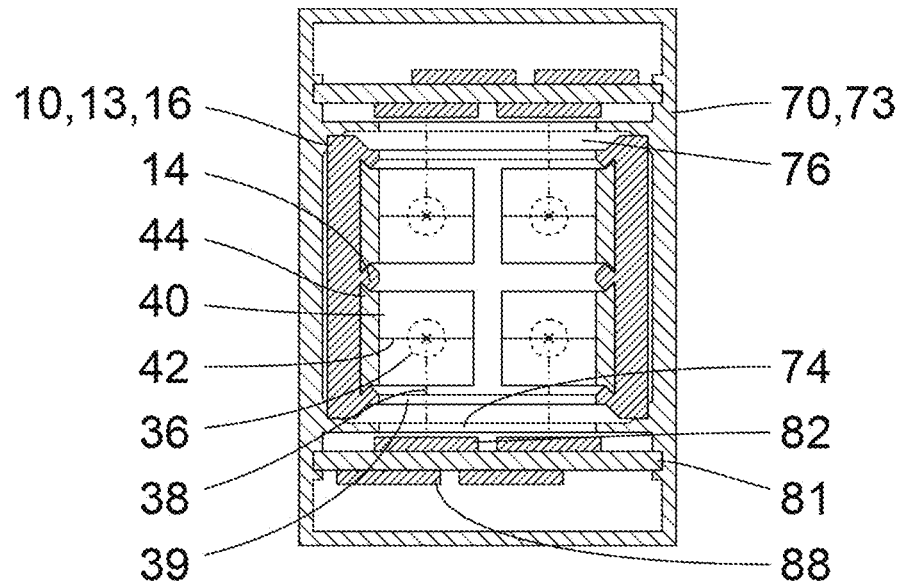
FIG. 7 shows a schematic representation of another image relaying device and another image detecting device.

FIG. 7 shows a schematic sectional representation of a further endoscope 10 and a further image detecting device 70. The sectional plane of FIG. 7 corresponds to the sectional planes of FIGS. 5 and 6. The configuration shown in FIG. 7 corresponds to the configurations shown in FIGS. 5 and 6 (all prisms 40 adjusted to the same longitudinal positions).

With respect to many features, characteristics and functions, the endoscope 10 and the image detecting device 70 shown in FIG. 7 are similar to the endoscopes and the image detecting devices, respectively, described above with reference to FIGS. 1 through 6. Below, in particular features, characteristics and functions of the endoscope 10 and the image detecting device 70 shown in FIG. 7 which are different from those of the endoscopes and the image detecting devices described above with reference to FIGS. 1 through 6 are described.

In contrast to the endoscopes described above with reference to FIGS. 1 through 6, the endoscope 10 shown in FIG. 7 comprises four parallel light paths formed by four parallel arrangements of rod lenses 36. Four similar prisms 40 are provided at four sliding carriages 42, each prism comprising a reflecting interface 42 bending the optical axis of the corresponding light path by 90 degrees.

The image detecting device 70 comprises four similar image sensors 82. Each of the image sensors 82 captures the images relayed by a corresponding rod lens 36 and reflected by a corresponding reflecting interface 42.

In the example shown in FIG. 7, a pair of image sensors 82 are arranged side by side at one printed circuit board 81, and another pair of image sensors 82 are arranged side by side at another printed circuit board 81, wherein both circuit boards are arranged at opposite sides of the recess 76. Correspondingly, the directions of propagation of light from an object to the image sensors 82 at the same printed circuit board are parallel, and the directions of propagation of light from an object to image sensors 82 at different printed circuit boards are anti-parallel. As in the variation to the embodiment of FIG. 6, a single image sensor with an active area of adequate dimensions to capture a pair of images traveling a parallel path may replace the two distinct image sensors 82. As an alternative, the image sensors 82 can be arranged at different positions, for example one image sensor 82 at each of four sides of the recess 76.

In the example shown in FIG. 7, the endoscope 10 comprises two window elements 39, and each window element 39 at the endoscope is provided for two parallel light paths. As an alternative, four separate windows can be provided, wherein each window element is allocated to one of the light paths of the endoscope 10 (similar to the embodiment described above with reference to FIG. 6).

In the example shown in FIG. 7, the image detecting device 70 comprises two window elements 74, and each window element 74 at the endoscope is provided for one pair of image sensors 82. As an alternative, four separate windows can be provided, wherein each window element is allocated to one of the image sensors 82.

In the example shown in FIG. 6, the endoscope 10 can, as an alternative, comprise a single window element 39 for both light paths (similar to the endoscope shown in FIG. 7) and/or the image detecting device 70 can comprise a single window element 74 for both image sensors 82 (similar to the image detecting device shown in FIG. 7).

Figure 8:
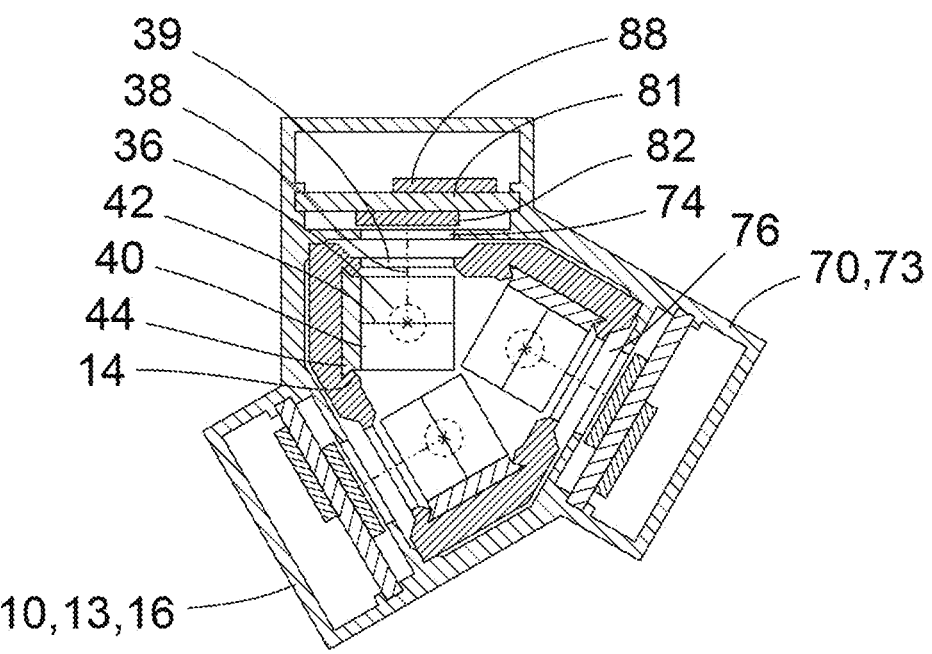
FIG. 8 shows a schematic representation of another image relaying device and another image detecting device.

FIG. 8 shows a schematic sectional representation of a further endoscope 10 and a further image detecting device 70. The sectional plane of FIG. 8 corresponds to the sectional planes of FIGS. 5 through 7. The configuration shown in FIG. 8 corresponds to the configurations shown in FIGS. 5 through 7 (all prisms 40 adjusted to the same longitudinal positions).

With respect to many features, characteristics and functions, the endoscope 10 and the image detecting device 70 shown in FIG. 8 are similar to the endoscope and the image detecting device, respectively, described above with reference to FIGS. 1 through 7. Below, in particular features, characteristics and functions of the endoscope 10 and the image detecting device 70 shown in FIG. 8 which are different from those of the endoscope and the image detecting device described above with reference to FIGS. 1 through 7 are described.

The endoscope 10 shown in FIG. 8 comprises three parallel light paths, each light path formed by a set of rod lenses 36 and a prism 40 comprising a reflecting interface 42. Correspondingly, the image detecting device shown in FIG. 8 comprises three image sensors 82 and three windows 74 allocated to the image sensors 82.

In the example shown in FIG. 8, the light paths' optical axes 38 downstream from the reflecting interfaces 42 are arranged tangentially, i.e. straight lines comprising the optical axes 38 downstream the reflecting interfaces 42 do not intersect in one but in three different points. As an alternative, the optical axes 38 downstream from the reflecting interfaces 42 can be arranged radially, i.e. straight lines comprising the optical axes 38 downstream the reflecting interfaces 42 intersect in a single point.

In particular in the latter case, the proximal end 16 of the endoscope 10 and the recess 76 of the image detecting device 70 can be designed such that the endoscope 10 can be easily rotated with respect to the image detecting device 70. For example, both the cross section of the proximal end 16 of the endoscope 10 and the cross section of the recess 76 of the image detecting device can be circular.

The same applies to the endoscope 10 and the image detecting device described above with reference to FIG. 7, in particular, when the optical axes 38 downstream from the reflecting interfaces 42 are arranged radially.

The number of image sensors 82 of each of the image detecting devices 70 shown in FIGS. 7 and 8 can be less than the number of light paths. In particular, the number of image sensors 82 may be two. The endoscope 10 can be rotated with respect to the image detecting device to different predetermined rotational positions in which the image sensors 82 are optically coupled to different pairs of light paths. When the endoscope's viewing direction is not parallel to the longitudinal axis of the shaft, rotation of the endoscope can rotate the viewing direction on a cone, and stereoscopic imaging in a number of different predetermined directions is facilitated.

In the examples shown in FIGS. 5 through 8, the rails 14 defining the paths of the sliding carriages 44 are dovetail guides. As an alternative, other linear guides or linear bearings can be provided.

In each of the examples shown in FIGS. 5 through 8, the image detecting device laterally encloses the proximal end 16 of the endoscope 10 completely. As an alternative, the cross section of the image detecting device can be U-shaped or C-shaped, thereby positively holding or locking the proximal end 16 of the endoscope 10 into a well defined position without completely enclosing it.

In all the endoscopes described above with reference to FIGS. 1 through 8, the reflecting interfaces 42 can be part of prisms, mirrors or other optical elements. The reflecting interfaces 42 and/or other surfaces of prisms 40 can be curved. The image sensors 82 can be integral with the optically transparent window elements 74.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:
1. An optical instrument comprising:
   A. an image relaying device, the image relaying device comprising
      1. a casing, the casing comprising
         a. a shaft region with a longitudinal axis; and
         b. a proximal end region comprising one or more optically transparent windows;
      2. two or more optical assemblies contained within the casing, each optical assembly comprising
         a. an objective lens at a distal end of the optical assembly;

b. an optical system to relay an image produced by the objective lens to a proximal region of the optical assembly, the optical system arranged substantially parallel to the longitudinal axis of the shaft region;

c. a reflecting means, the reflecting means directing the image relayed by the optical system to be detected through one of the optically transparent windows; and d. an adjustment means, the adjustment means adjusting the position of the reflecting means along an axis essentially parallel to the longitudinal axis of the shaft, and thereby adjusting the optical path length between the objective lens and the reflecting means; and B. an image detecting device removeably coupled to the proximal end region of the image relaying device, the image detecting device comprising:

1. one or more window elements; and 2. one or more image sensors, each image sensor having one or more image sensor active areas lying in a direction essentially parallel to the longitudinal axis of the shaft, positioned to capture one or more images relayed by the two or more optical assemblies through the image relaying device windows and corresponding image detecting device windows, wherein each adjustment means adjusts the position of the corresponding reflecting means laterally along the longitudinal axis of the shaft and relative to the position of its corresponding image sensor.

2. The optical instrument of claim 1 wherein each of the reflecting means of the image relaying device further comprises a position indication means, and the image detecting device further comprises one or more receivers for receiving, from corresponding position indication means, information representing the position of the corresponding reflecting means of the corresponding image relaying device.

3. The optical instrument of claim 1 wherein the adjustment means comprises a sliding carriage slidably fixed to a rail rigidly connected to the casing.

4. The optical instrument of claim 1 wherein the position of the reflecting means is adjusted by the adjustment means so as to produce an in-focus image on the image sensor.

5. The optical instrument of claim 1 wherein each of the associated adjustment means for each of the optical assemblies is so adjusted such that each optical assembly produces an in-focus image at its respective image sensor.

6. The optical instrument of claim 1 wherein the two or more optical assemblies produce two or more distinct images on a single image sensor.

7. The optical instrument of claim 1 wherein the casing is hermetically sealed.

8. The optical instrument of claim 3 further comprising a support rigidly connected to or integral with the casing, and wherein the adjustment means further comprises an adjusting screw, the adjusting screw in threaded contact with the carriage and having an end in contact with the support.

9. The optical instrument of claim 8 wherein the adjustment means further comprises a spring under compression having a first end in contact with the support and a second end in contact with the carriage.

10. The optical instrument of claim 9 wherein the first end of the spring under compression is in contact with the support on a side opposite the side of the support in contact with the screw.

11. The optical instrument of claim 2 wherein the image detecting device further comprises data processing circuits receiving position indication data from the position indication means representing the position of the corresponding reflecting means of the corresponding image relaying device.

12. The optical instrument of claim 11 further comprising an image evaluating circuit, the image evaluating circuit calculating from an image data received from the one or more image sensors a difference in the positions of the reflecting means, and providing corresponding position information to the data processing circuits or to the image sensors.

13. The optical instrument of claim 11 wherein the data processing circuits comprise a frame positioning circuit, the frame positioning circuit determining, using the position indication data of the position of the reflecting means, regions of the respective image sensor wherein image data is collected.

14. The optical instrument of claim 13 wherein the image processing circuits discard data not referring regions of the respective image sensor wherein image data is not collected.

* * * * *